(12) United States Patent
Zanelli et al.

(10) Patent No.: US 7,815,633 B2
(45) Date of Patent: Oct. 19, 2010

(54) HAIR REMOVAL USING FOCUSED HIGH INTENSITY ACOUSTIC ENERGY

(75) Inventors: Claudio I. Zanelli, 2100 Prospect St., Menlo Park, CA (US) 94025; Samuel M. Howard, Mountain View, CA (US)

(73) Assignee: Claudio I. Zanelli, Menlo Park, CA (US)

( * ) Notice: Subject to any disclaimer, the term of this patent is extended or adjusted under 35 U.S.C. 154(b) by 140 days.

(21) Appl. No.: 12/156,870

(22) Filed: Jun. 4, 2008

(65) Prior Publication Data

US 2008/0242990 A1 Oct. 2, 2008

Related U.S. Application Data

(63) Continuation of application No. 10/756,173, filed on Jan. 12, 2004, now abandoned.

(51) Int. Cl.
*A61B 18/04* (2006.01)
(52) U.S. Cl. .......................................... 606/27; 606/28
(58) Field of Classification Search .................. 606/32, 606/33, 36, 41, 43, 27, 28; 601/1–3
See application file for complete search history.

(56) References Cited

U.S. PATENT DOCUMENTS

| | | | |
|---|---|---|---|
| 5,368,032 A * | 11/1994 | Cline et al. ................. 600/411 |
| 5,769,790 A | 6/1998 | Watkins et al. ............... 600/439 |
| 5,906,609 A * | 5/1999 | Assa et al. ...................... 606/9 |
| 6,200,326 B1 | 3/2001 | Narayanan et al. .......... 427/162 |
| 6,432,067 B1 | 8/2002 | Martin et al. ................... 601/2 |
| 6,595,934 B1 | 7/2003 | Hissong et al. ............. 428/690 |
| 6,719,694 B2 * | 4/2004 | Weng et al. ................. 600/439 |
| 2003/0060810 A1 * | 3/2003 | Syrowicz et al. ............... 606/9 |
| 2003/0083536 A1 | 5/2003 | Eshel et al. ................. 428/569 |
| 2005/0143677 A1 | 6/2005 | Young et al. .................... 601/2 |
| 2005/0154381 A1 * | 7/2005 | Altshuler et al. ............... 606/9 |

FOREIGN PATENT DOCUMENTS

| | | |
|---|---|---|
| WO | WO 02/09813 | 2/2002 |
| WO | WO 02/054018 | 7/2002 |

\* cited by examiner

*Primary Examiner*—Roy D Gibson
(74) *Attorney, Agent, or Firm*—Shirley L. Church

(57) ABSTRACT

Hair is permanently removed from a patient's skin by transcutaneously focusing high intensity acoustic energy at a hair follicle and applying sufficient energy to destroy the follicle, whereby hair is removed and regrowth is prevented. Typically, a region of a patient's skin would be ultrasonically imaged to show the location of a plurality of individual hair follicles. The individual imaged hair follicles are then treated using a system which automatically directs the high intensity acoustic energy at each follicle.

16 Claims, 5 Drawing Sheets

HAIR REMOVAL USING FOCUSED HIGH INTENSITY ACOUSTIC ENERGY

This application is a Continuation Application of U.S. patent application Ser. No. 10/756,173, filed Jan. 12, 2004, and entitled: "Methods and Systems for Removing Hair Using Focused Acoustic Energy", which is currently pending.

BACKGROUND OF THE INVENTION

1. Field of the Invention

The present invention relates generally to medical methods and devices. More particularly, the invention relates to methods and systems for removing hair by ablation of hair follicles.

Over the years, hair removal has been accomplished by a variety of temporary and permanent techniques. Tweezers, wax, sticky tape, and similar methods have been used to pull hair from its root beneath the skin. Such hair removal, however, is only temporary and the hair will soon regrow in the same location. Permanent hair removal may be accomplished by destroying the hair follicle which provides for new hair growth. The most common methods for achieving such permanent hair removal are electrolysis and the use of short pulsed light. Electrolysis requires inserting a wire into the same pore as the hair, advancing the wire until the operator feels some resistance caused by the hair follicle, and then applying an electric pulse. The electric pulse destroys the follicle preventing regrowth after the hair falls out. While effective, the introduction of a needle into the pore is uncomfortable for the patient, requires a high degree of skill by the operator, and is very time-consuming.

In contrast, short light pulses can be used to illuminate patches of skin at high intensity to heat and destroy all the hair present in that patch. While representing an enormous saving of time, the light functions by transmitting heat through the individual hairs to the hair follicle. Due to differences in skin and hair pigmentation, the results of such heat generation and absorbance can be highly variable, and the method is not successful in patients with dark skin, light hair color, or on very fine hair of any color.

A third technique has recently been proposed in U.S. Pat. No. 6,200,326. Instead of delivering electrical energy through a needle, ultrasonic energy may be delivered to individual hair follicles by advancing a needle through a pore to a hair follicle. While potentially effective, this method suffers from the same drawbacks and disadvantages discussed above with respect to hair removal by needle electrolysis.

For these reasons, it would be desirable to provide alternative and improved methods for permanently removing hair from a patient's skin. It would be particularly desirable if such methods and systems could destroy hair follicles without the need to introduce a needle or other apparatus through the associated hair pores and without relying on thermal or other energy transmission properties of the individual hairs. Such methods and systems should preferably be relatively simple to use and not require extensive training on the part of operators. Additionally, it would be particularly desirable if the methods could treat hair follicles which, at the time of the procedure, are in their telogen phase or without hair for other reasons. At least some of these objectives will be met by the inventions described hereinbelow.

2. Description of the Background Art

Use of a needle to deliver ultrasonic energy to disrupt hair follicles is described in U.S. Pat. No. 6,200,326 B1. Skin rejuvenation by ablating a plurality of subcutaneous sites with an array of ultrasonic transducers is described in U.S. Pat. No. 6,595,934 B1. Lysing adipose tissue using an externally focused high energy ultrasound transducer is described in U.S. Patent Application Publication No. 2003/0083536A1 and WO 02/054018A2. The full disclosures of each of these prior publications are incorporated herein by reference.

BRIEF SUMMARY OF THE INVENTION

The present invention provides improved and alternative methods and systems for permanent hair removal. By transcutaneously focusing high intensity acoustic energy at hair follicles beneath the skin, the hair follicles may be individually destroyed to both remove the hair and prevent its regrowth. Usually, prior to ablation, the hair follicles will be imaged and mapped to facilitate subsequent delivery of the high intensity acoustic energy, typically using automated methods and systems. Conveniently, the imaging and ablation may be performed with the same transducer in order to simplify both the method and the system for performing the method.

In a first aspect of the method of the present invention, hair is removed from a patient's skin by focusing high intensity acoustic energy upon hair follicles beneath the skin. According to one embodiment, the acoustic energy is focused at predetermined follicle locations where those locations are typically determined by acoustic imaging. Transcutaneously focusing the ablative energy may comprise adjusting the depth of the focal region. In a first instance, this depth may be adjusted by translating the ablative transducer along a line towards or away from the skin surface. In a second instance, the depth may be adjusted by changing the curvature of the surface of the ablative transducer. In a third instance, the depth may be adjusted by controlling the operation of a phased array ablative transducer. Usually, the high intensity acoustic energy if focused at a depth in the range from 1 mm to 6 mm, usually from 2 mm to 4 mm, and with a minimum beam width in the range from 0.05 mm to 0.5 mm, preferably from 0.1 mm to 0.2 mm. The high intensity acoustic energy will be delivered under conditions selected to raise the temperature at the hair follicle to at least 50° C., preferably at least 60° C., for a time period of at least 0.05 seconds, and more preferably at least 0.1 seconds. Usually, the ablative energy is delivered to each follicle in an amount in the range of from 0.1 J to 10 J and often from 1 J to 5 J, depending at least in part on the volume of the follicle and the time of delivery.

In a second aspect of the method of the present invention, hair is permanently removed from a patient's skin by first scanning an acoustic transducer over the skin surface to identify locations of the hair follicles beneath the skin. High intensity acoustic energy is then transcutaneously focused at least some of the identified follicle locations, typically using an acoustic transducer, more typically using the same acoustic transducer that was used to identify locations of the hair follicles.

In a third aspect of the method of the present invention, a transducer platform is immobilized over a target area of the patient's skin. An acoustic transducer is scanned over the skin to determine the locations beneath the skin of hair follicles, where the locations are determined relative to the immobilized transducer platform. An acoustic transducer is then positioned over the skin at least some of the predetermined locations, again relative to the immobilized platform which acts as a fixed reference frame in performing the method. High intensity acoustic energy is then transcutaneously focused at individual hair follicles from the positioned acoustic transducer. Usually, the acoustic transducer which is used to determine the hair follicle location will be the same transducer which is used to focus the high intensity acoustic energy at the hair follicles. Typically, the platform will provide a drive system which permits the mechanical advancement of the transducer in X- and Y-directions over an imaging plane to known coordinates. Thus, the initial imaging step can be performed while tracking the precise position of the transducer using the drive system, typically a servo-controlled positioning system. The same positioning system can be used to subsequently position the same transducer at the identified locations to deliver the high intensity acoustic energy in order to perform the hair removal according to the present invention.

The present invention still further provides systems for hair removal. The systems include a transducer selectively operable to imaged hair follicle locations and to acoustically ablate hair follicles at said imaged locations. Means for tracking the location of the transducers over the patient's skin are provided and interfaced with a controller for acquiring image data from the transducer and directing high intensity acoustic energy to follicles selected from among those imaged by the system.

The tracking means preferably comprises a transducer platform, which is typically in the form of a hand piece, adapted to be engaged against the patient's skin. A drive system within the platform advances the transducer over a planar region defined by a window or other structure within the platform. In this way, the position of the transducer can both be selected and recorded while imaging is being performed, thus facilitating reaccessing of the imaged follicles during the ablation portion of the procedure. Typically, the drive system can be a conventional X-Y motion positioner, such as the type used in printers and printer-plotter mechanisms. The positioner should be repeatable to at least +/−0.05 mm, more preferably +/−0.01 mm. Also preferably, the transducer platform will include an adhesive, abrasive, a suction or aspiration channel, or other modification for temporarily adhering to the patient's skin. In this way, the platform may be immobilized relative to the skin location during both the imaging and acoustic ablation portions of a procedure. By preferably placing the adhering material about the treatment window or other access region of the platform, the skin may also be tightened to remain relatively taught over the area which is scanned and subsequently treated.

DETAILED DESCRIPTION OF THE INVENTION

Figure 1:
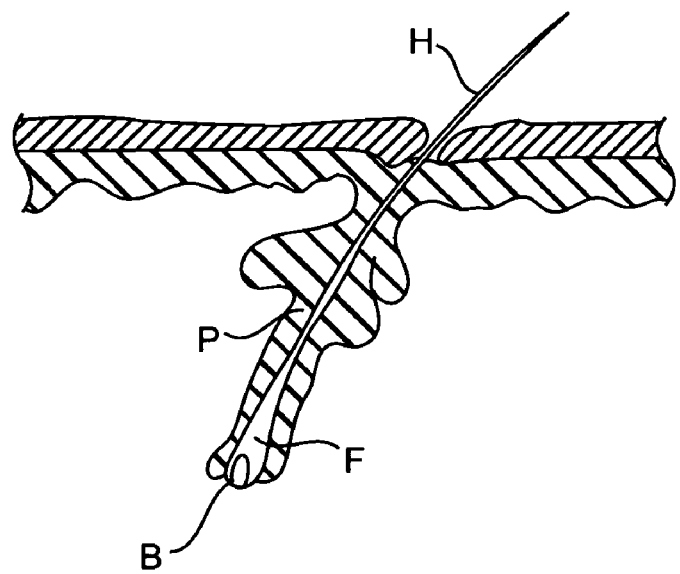
FIG. 1 is a cross-sectional illustration of a hair showing a hair follicle at the end of the pore through the skin.

Referring to FIG. 1, the anatomy and physiology of a hair follicle will be described. The hair follicle passes through a growth cycle beginning with an active phase (anagen), a transformation phase (catagen), and a resting phase (telogen). During anagen, the hair actively grows from a matrix of cells in the base of the follicle F called the bulb B. In the center of the bulb is the dermal papilla, which provides blood to the matrix cells. During catagen, the matrix cells become inactive and atrophy, causing the root of the hair to detach from the matrix cells and the dermal papilla. During the telogen phase, the hair is dead and tends to fall out. Before a new hair can grow, new matrix cells must begin to form around the dermal papilla, and the follicle must reattach to those new matrix cells. Once this transformation is complete, the follicle F has completed its cycle and is reformed into the anagen phase. Thus, during the anagen and catagen phases, the growth sources are found in the bulb of the follicle. During the telogen phase, in contrast, there is no active growth, and there is no follicle bulb. The cells that are responsible for future growth are located around the dermal papilla.

As used herein and in the claims, the phrase "hair follicle" will be intended to include both the active hair follicle present in the anagen and catagen phases. For simplicity, however, the phrase will also be intended to cover the site of the future hair follicle in the region of the dermal papilla during the telogen phase of hair growth. The methods of the present invention for applying high intensity acoustic energy to the region of the hair follicle work both with the actual follicles and with the matrix cells and the dermal papilla which would, if not ablated, result in subsequent re-growth of the follicle and related hair.

Figure 2:
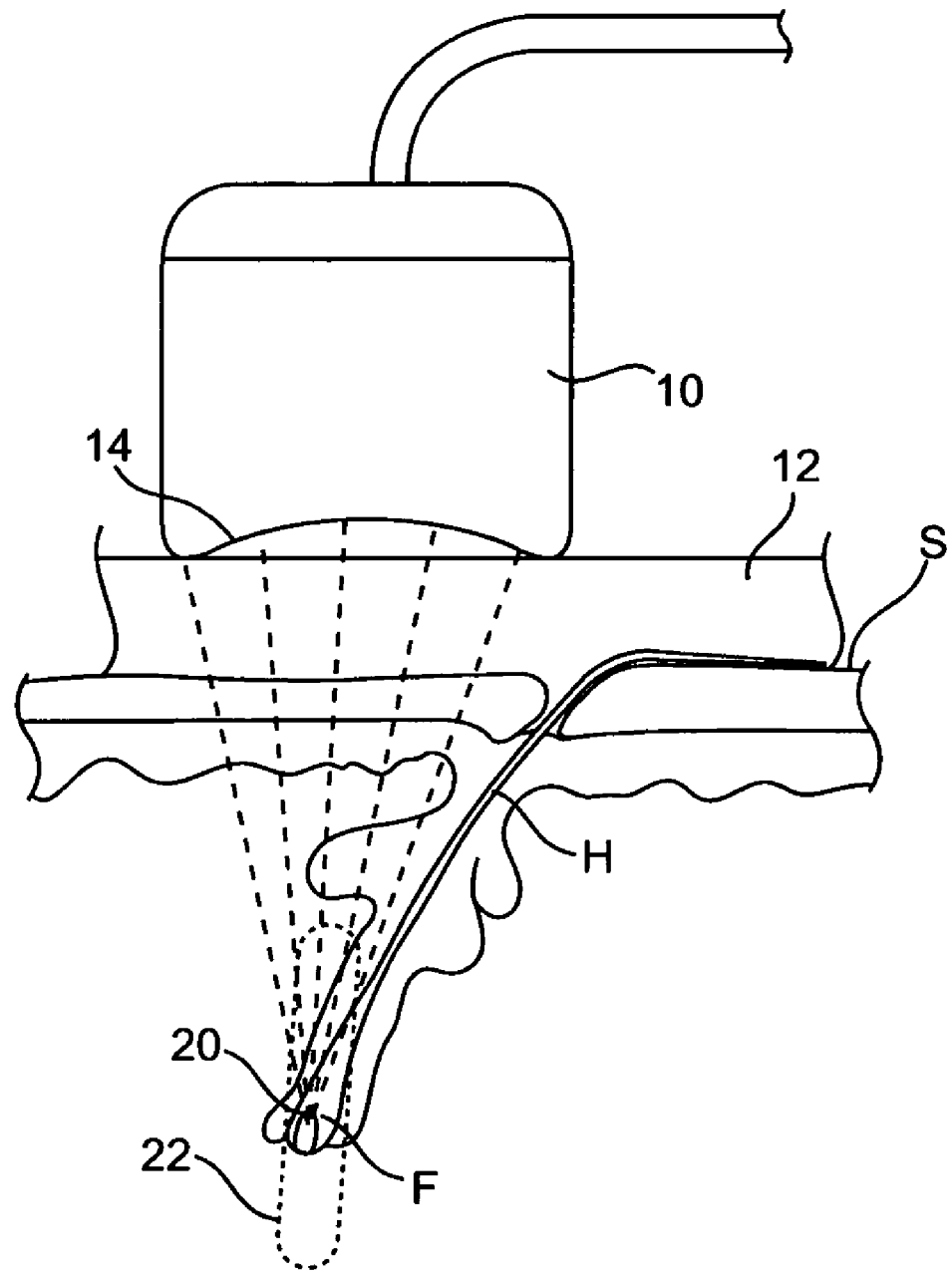
FIG. 2 illustrates a transducer delivering high intensity acoustic energy destroying a hair follicle according to the methods of the present invention.

Referring to FIG. 2, the present invention relies on the transcutaneous focusing of high intensity acoustic energy, typically ultrasonic energy, to the follicle F of the hair H. By "transcutaneous focusing," it is meant that a transducer 10 or other suitable source of high intensity acoustic energy is located at or near the surface of the patient's skin S. As illustrated in FIG. 2, the transducer 10 is placed over a layer of acoustic coupling medium, such as an acoustic gel 12, and the transducer surface 14 is adapted to focus the high intensity acoustic energy at a depth and location 20 which is located at the follicle F. The focusing of the acoustic ablative energy will typically create a region of heating, shown by a broken line 22, which encompasses the follicle as well as the associated dermal papilla and matrix cells. The width and depth of focus of energy has been described above. The high intensity energy will be applied for a time sufficient to raise the temperature about the follicle sufficiently high to ablate the follicle and/or other cells responsible for hair growth in that region.

Figure 3:
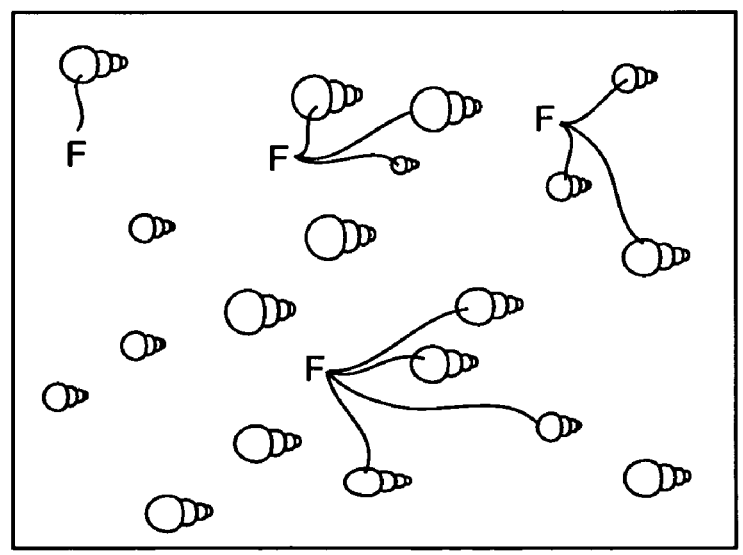
FIG. 3 illustrates a planar region of a patient's skin showing how the hair follicles would appear under acoustic imaging.

While it would be possible to manually locate a transducer 10 at regions more or less above individual hair follicles in order to ablate individual hair growth, such manual methods would be extremely tedious and time-consuming (although not necessarily more difficult and time-consuming than those of the prior art). In order to increase the effectiveness of the methods of the present invention and reduce the time required to perform them, systems according to the present invention will preferably provide for both automated imaging of the target hair follicles as well as positioning of the ablative transducers in order to deliver energy to said hair follicles. For example, as shown in FIG. 3, ultrasonic scanning and imaging of a patient's skin may reveal the presence of individual hair follicles F beneath the patient's skin. Note that the image of the individual hairs and hair follicles will appear generally as spots of various sizes, depending on the width of the acoustic beam at the depth of the scan. By overlaying different depth data on the same image, encoded by color or other distinguishable feature, it is possible to visualize the range of depths for each hair, thus determining the maximum depth of each follicle. The use of the combined positional and depth information for the individual hair follicles will be relied on by the methods and systems of the present invention for selectively applying and delivering the high intensity acoustic energy to the hair follicles, as described in more detail below.

Figure 4:
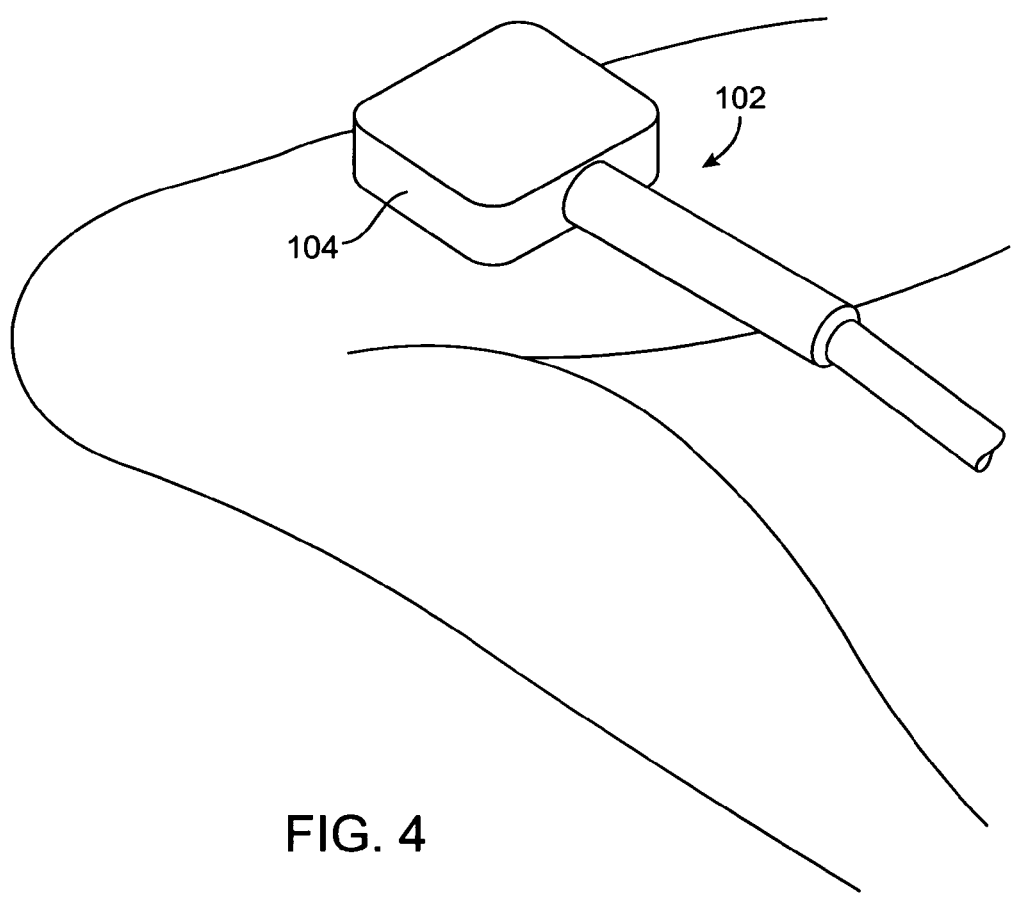
FIGS. 4-6 illustrates a system constructed in accordance with the principles of the present invention for imaging and acoustic ablative removal of hair.
Figure 5:
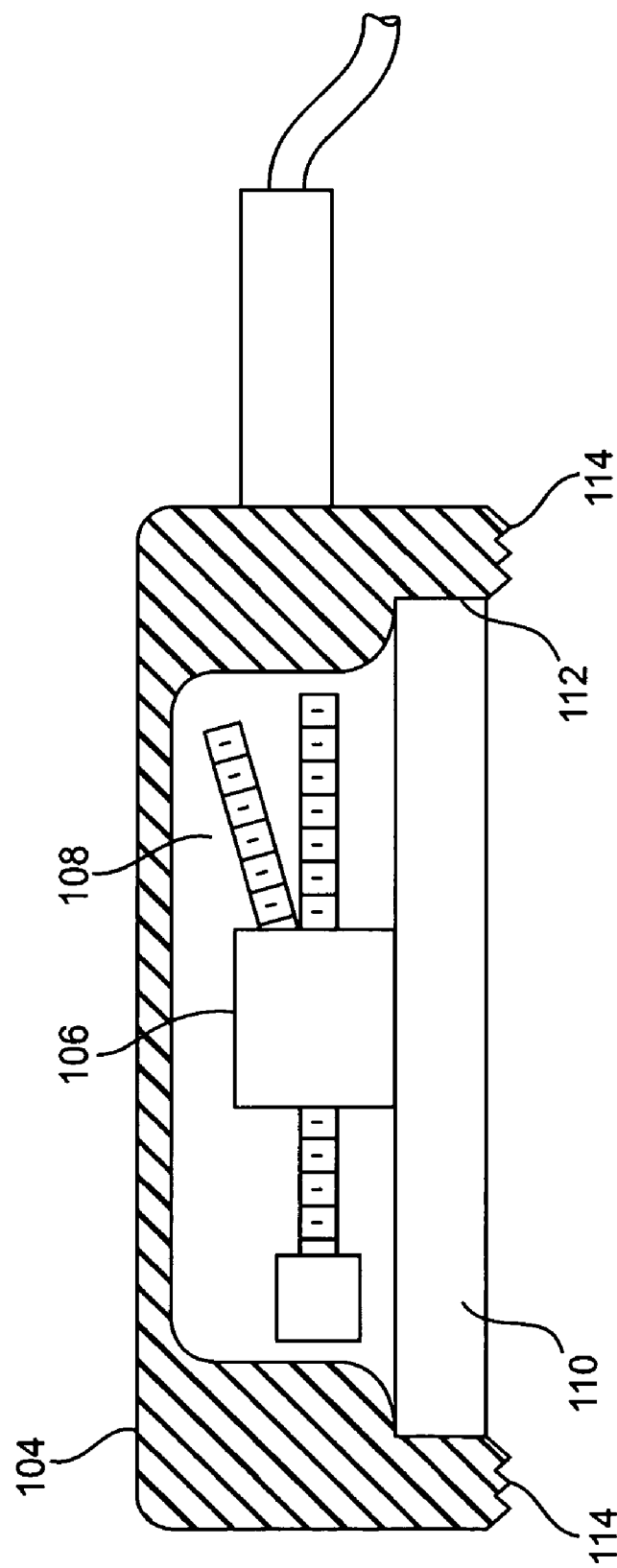
Figure 6:
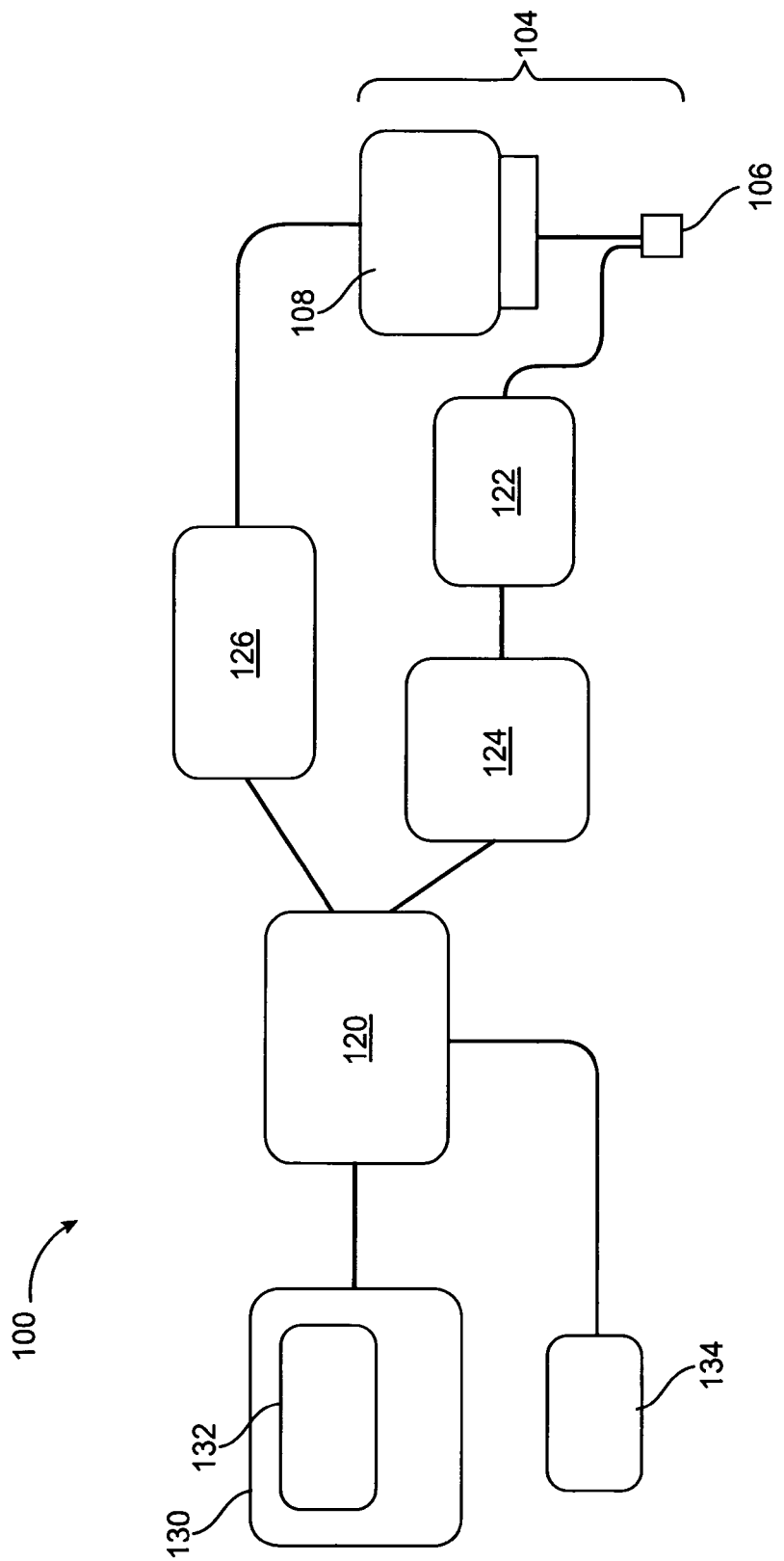

A system 100 useful for both for imaging and delivering high intensity acoustic energy to hair follicles according to the methods of the present invention is illustrated in FIGS. 4-6. The systems will conveniently comprise a platform or handpiece 102 including a head 104 which is adapted to be placed against a region of the patient's skin which is to be treated. Typically, the head 104 includes a transducer 106 which is mounted in a X-/Y-drive system, as illustrated in FIG. 5. The transducer will thus be positionable over a coupling medium 110 which is formed in a lower window 112 of the device housing. Preferably, an adhesive, abrasive, or other adhering region 114 is formed about the coupling medium 110 to facilitate placement and immobilization of the scan head 104 on the skin. The coupling material can be a liquid encapsulated by a membrane that contacts the tissue. Alternatively, it may be a gel of semi-rigid nature that contacts the tissue either directly or through a membrane. The coupling material should have an acoustic impedance similar to that of tissue (1.5 Mrayls) and a sound velocity similar to tissue (1540 m/s).

The scan head 104 is able to move the transducer 106 over a plane orthogonal to the direction of the acoustic beam, thus permitting scanning of the skin being treated. Scanning is driven by a controller 120 (FIG. 6) which automatically initiates scanning and records position and depth information for each hair follicle for imaging purposes. In particular, the controller operates a pulse/receiver 122 which operates the transducer. Data from the transducer is collected in a data acquisition system 124, while all mechanical motion of the scan head is controlled by a motor interface 126. Optionally, a display 130 can permit the operator to observe the imaged follicles in plan view, for example as shown in FIG. 3, through a screen 132. The user may then select which of the imaged follicles is to be ablated using a keyboard or other interface unit 134.

Once the scanning is completed, and the operator has optionally identified those follicles which are to be ablated, the treatment data may be compiled including the locations and depths of each hair follicle to be ablated. At that point, the system can begin automated ablation of the hair follicles. The controller 120 can position the transducer 106 sequentially at each follicle to be treated. The pulse/receiver will now drive the transducer to deliver a high energy burst which is focused at the hair follicle in order to kill any cells at the follicle or within the dermal papilla. The killing occurs by heating the tissue to a minimum temperature, typically at least 55° C., for a time of at least 0.01 seconds.

By firmly adhering the scan head to the skin during both the imaging and ablation phases of the treatment protocols, accurate positioning of the transducer for ablation is assured. Optionally, the system could be provided with image recognition software which would permit automated positioning and confirmation of position of the transducer 106. The information could be used for either fine positioning of the transducer or as an alert should it appear that the transducer is mispositioned.

The depth of focus of the transducer can be controlled in several ways. In the case of a phased array transducer, the depth can be electronically controlled. For single element transducers, the depth can be controlled either by controlling the vertical position of the transducer over the skin surface (e.g. by adding more or less coupling material between the transducer and the skin), or alternatively some transducers may be provided with emitting surfaces that have a curvature which may be adjusted to control depth of focus.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of removing hair and dermal papilla regions from and beneath a patient's skin, said method comprising:
   immobilizing a platform over a target area of said patient's skin;
   scanning said target area using an acoustic transducer mounted on said platform to determine depth and location beneath said skin of a plurality of hair follicles or dermal papilla regions, or a combination thereof relative to said immobilized platform;
   producing a tangible image of said scanned hair follicle or dermal papilla locations, or a combination thereof;
   designating which of a plurality of hair follicles or dermal papilla regions, or combinations thereof identified in said tangible image are to be ablated;
   positioning an acoustic transducer over said skin at a determined location relative to said immobilized platform;
   focusing high intensity acoustic energy transcutaneously at said depth and location of each hair follicle or dermal papilla region to be removed, wherein said acoustic energy is generated from an acoustic transducer positioned on said platform; and
   applying to each hair follicle or dermal papilla region to be removed sufficient high intensity acoustic energy to destroy said hair follicle or dermal papilla region.

2. A method as in claim 1 wherein scanning comprises mechanically advancing the transducer in X- and Y-directions over an imaging plane to known coordinates.

3. A method as in claim 2, wherein positioning an acoustic transducer comprises mechanically advancing the transducer in X- and Y- directions to the same coordinates.

4. A method as in claim 1, wherein said focusing of said high intensity acoustic energy transcutaneously includes adjusting a depth of focus by translating said acoustic transducer along a vertical line.

5. A method as in claim 1, wherein said focusing of said high intensity acoustic energy transcutaneously includes adjusting a curvature of a transducer surface.

6. A method as in claim 1, wherein said transcutaneously focusing of said high intensity acoustic energy includes adjusting a depth of focus by controlling the operation of a phased array transducer.

7. A method as in claim 1, wherein said high intensity acoustic energy is focused at a depth beneath the skin in the range from 1 mm to 6 mm and at a width in the range from 0.1 mm to 0.3 mm.

8. A method as in claim 7, wherein said high intensity acoustic energy is delivered under conditions selected to raise the temperature at the hair follicle to at least 50° C. for a time of at least 0.1 sec.

9. A method as in claim 8, wherein said high intensity acoustic energy is delivered in an amount from 0.1 J to 10 J to said at least one hair follicle.

10. An apparatus used in hair removal from a skin surface and prevention of regrowth, said apparatus comprising:
   a transducer selectively operable to image a plurality of hair follicle and dermal papilla region locations and to acoustically ablate hair follicles and dermal papilla at imaged locations;
   means of tracking a position of the transducer over said skin surface;
   a controller which acquires image data from the transducer including the depth and location of each hair follicle and dermal papilla region, and which directs high intensity acoustic energy to the depth and location of at least a portion of said imaged hair follicle or dermal papilla region locations;

a display which provides a visual depiction of said plurality of imaged hair follicle or dermal papilla region locations; and means for a user to designate which of said plurality of hair follicles and dermal papilla regions in the visual depiction are to be ablated.

11. An apparatus as in claim 10, wherein the tracking means comprises:

a transducer platform adapted to be engaged against the patient's skin; and a drive device for advancing the transducer over a planar region defined by the platform, wherein the position of the transducer can be both selected and recorded.

12. An apparatus as in claim 11, wherein the drive device is an X-Y motion positioner.

13. An apparatus as in claim 12, wherein the X-Y motion positioner is repeatable to ±0.01 mm.

14. An apparatus as in claim 10, wherein high intensity acoustic energy is applied at a depth beneath the skin in the range from 1 mm to 6 mm and at a width in the range from 0.1 mm to 0.3 mm.

15. An apparatus as in claim 14, wherein high intensity acoustic energy is delivered under conditions selected to raise the temperature at selected hair follicle locations to at least 50° C. for a time of at least 0.1 sec.

16. An apparatus as in claim 14, wherein the ablative energy is delivered in an amount from 0.1 J to 10 J to said at least one hair follicle.

* * * * *